US00PP30382P3

(12) United States Plant Patent
Olesen

(10) Patent No.: US PP30,382 P3
(45) Date of Patent: Apr. 16, 2019

(54) MINIATURE ROSE PLANT NAMED 'POULPAR094'

(50) Latin Name: *Rosa hybrid*
Varietal Denomination: Poulpar094

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/330,304

(22) Filed: Sep. 6, 2016

(65) Prior Publication Data

US 2018/0116081 P1 Apr. 26, 2018

(51) Int. Cl.
*A01H 5/02* (2018.01)
*A01H 6/74* (2018.01)

(52) U.S. Cl.
USPC ..... Plt./128
CPC ..... *A01H 5/02* (2013.01); *A01H 5/0222* (2013.01); *A01H 6/749* (2018.05)

(58) Field of Classification Search
USPC ..... Plt./123, 128
See application file for complete search history.

(56) References Cited

PUBLICATIONS

UPOV-PLUTO: Plant Variety Database; citation for 'Poulpar094'.*

* cited by examiner

*Primary Examiner* — Susan Beth McCormick Ewoldt

(57) ABSTRACT

A new garden rose plant of the Miniature class which has abundant, deep pink flowers and attractive foliage. This new and distinct variety has shown to be uniform and stable in the resulting generations from asexual propagation.

3 Drawing Sheets

Botanical designation: *Rosa* hybrid.
Variety denomination: 'Poulpar094'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar094', originated as a single seedling from the stated cross.

The new variety may be distinguished from its male pollen parent and female seed parent primarily by the following characteristics. The male pollen parent plant has red flowers, while the new variety has deep pink flowers. The female seed parent plant has medium pink flowers, while the new variety has deep pink flowers.

The objective of the hybridization of this rose variety was to create a new and distinct variety for garden use with unique qualities, such as:

1. Uniform and abundant deep pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar094' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar094' was selected in the spring of 2008 by the inventor as a single plant from the progeny of the aforementioned hybridization.

Asexual reproduction of 'Poulpar094' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpar094' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar094'.

DETAILED DESCRIPTION OF THE VARIETY

Figure 1:
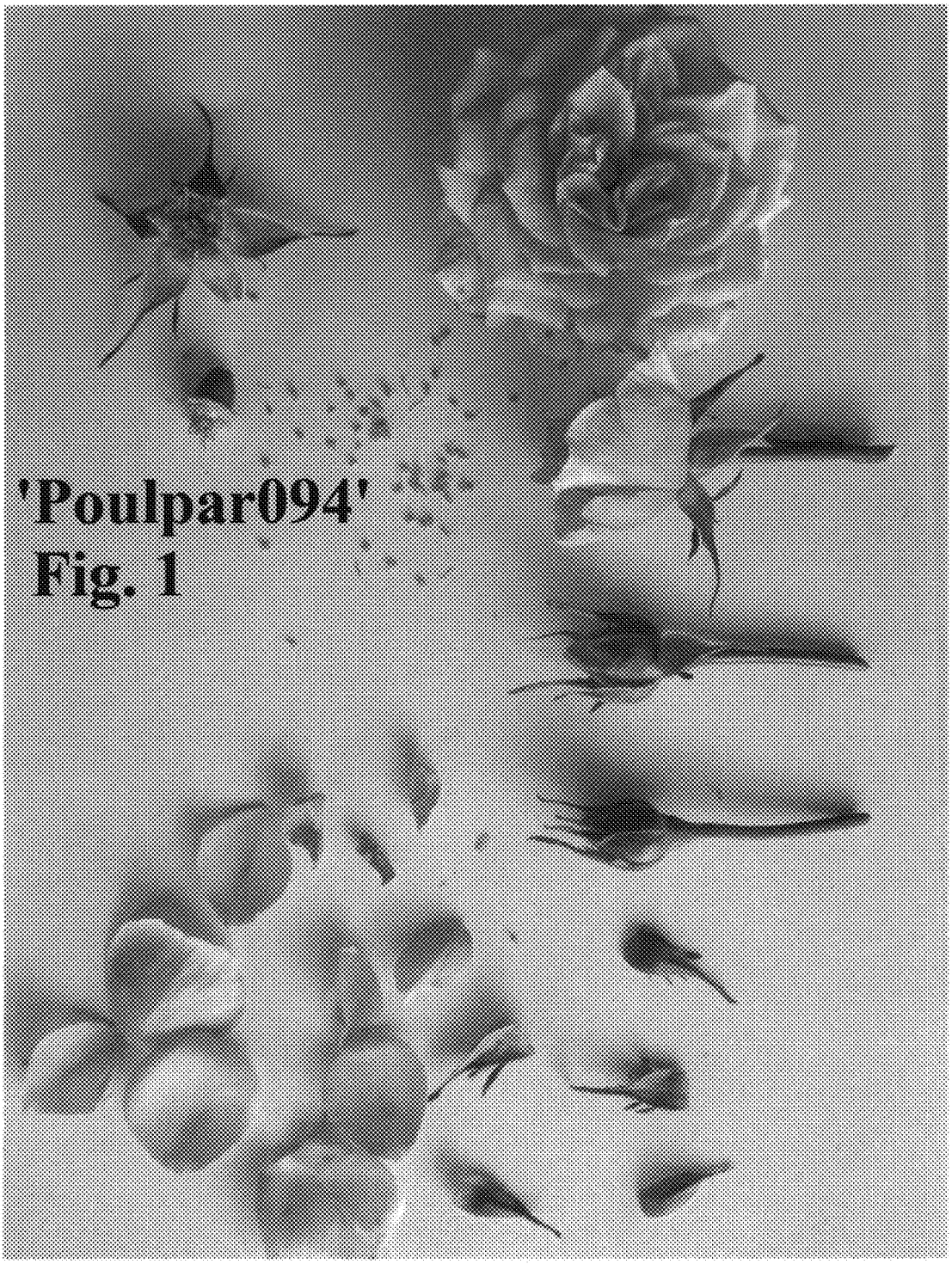
FIG. 1 shows flowers at various stages of development, petals detached, sepals, and reproductive flower parts.
Figure 2:
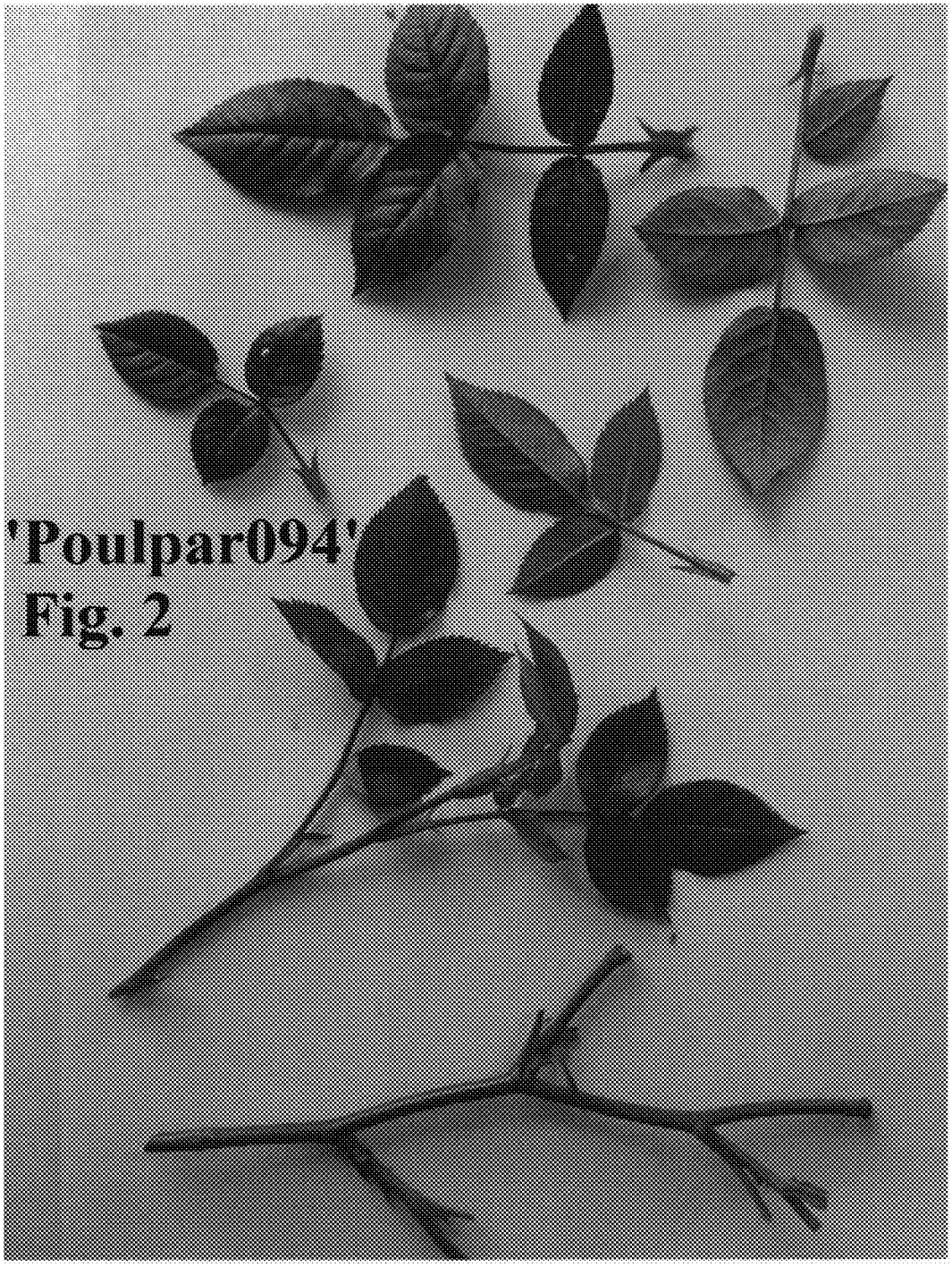
FIG. 2 shows mature leaves, juvenile leaves, and bare stem.
Figure 3:
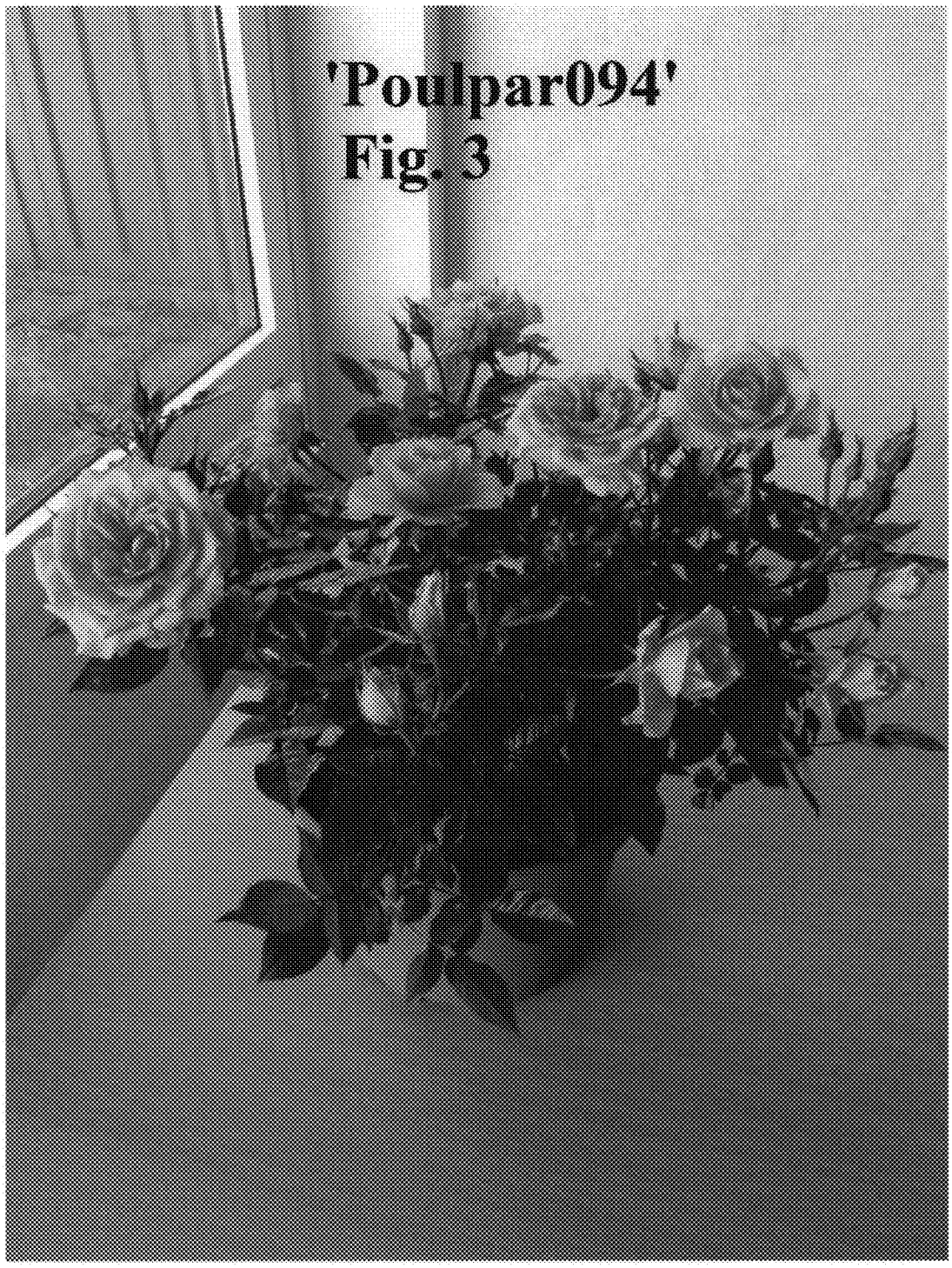
FIG. 3 shows the entire plant in flower. Illustrated plants are 1 year of age.

The following is a description of 'Poulpar094', as observed in its growth in a container nursery in Odense Denmark. Observed plants are 1 year of age, and were grown on their own roots in 23 cm containers. Color references are made using The Royal Horticultural Society (London, England) Colour Chart, 2001, except where common terms of color are used.

For a comparison, several physical characteristics of the rose variety 'Poulhi008', U.S. Plant Pat. No. 15,722 are compared to 'Poulpar094' in Chart 1.

CHART 1

| | 'Poulpar094' | 'Poulhi008' |
|---|---|---|
| Petal Count | 40 | 40 to 45 |
| Flower Diameter | 75 mm | 80 mm |
| General Tonality of Flower Color | Red-Purple Group 62A | Red Group 55B |

FLOWER AND FLOWER BUD

Blooming habit: Continuous.

Flower bud:

*Size*.—Upon opening, 30 mm in length from base of receptacle to end of bud. Bud diameter is 14 mm.

*Bud form*.—Ovoid.

*Bud color*.—As sepals divide petals are Red Group 38A.

*Sepal inner surface*.—Color: Yellow-Green Group 147C. Surface: Lightly pubescent.

*Sepal outer surface*.—Color: Yellow-Green Group 146C with intonations of Red-Purple Group 183B. Texture: Slightly rough.

*Sepal shape*.—Apex: Cirrhose. Base: Flat at union with receptacle.

*Sepal margin*.—Margins have weak foliaceous appendages on three of the five sepals.

*Sepal size*.—25 mm long, 10 mm wide.

*Receptacle*.—Texture: Smooth. Size: 7 mm in height, 8 mm wide. Color: Yellow-Green Group 144B. Shape: Funnel.

*Pedicel*.—Surface: Smooth. Length: 25 to 45 mm. Diameter: 3 mm on average. Color: Yellow-Green Group 144A with intonations of Greyed-Purple Group 183B. Strength: Strong.

*Peduncle*.—Length: 4 to 12 to cm. Diameter: About 4 mm. Color: Yellow-Green Group 146A with weak intonations of Greyed-Purple Group 183B. Texture: Smooth.

Flower bud development: Flower buds are borne in clusters of 1 to 5 flower buds per stem. Development as a panicle.

Flower bloom:

*Fragrance*.—None.

*Duration*.—The blooms have a duration on the plant of approximately 7 to 10 days. Petals fall cleanly away from plant after flowers have fully matured.

*Size*.—Flower diameter is 75 mm when open. Flower depth is 35 mm.

*Flower shape*.—Rosette double flower with many slightly overlapping petals of different sizes.

*Shape of flower, side view*.—The upper portion is a flattened convex. The lower portion is flat.

Petalage: Under normal conditions, flowers have 40 petals.

General tonality of flower: Open flowers are Red-Purple Group 62A.

Petal color:

*Upon opening, outer petals*.—Upper surface: Red-Purple Group 62B. Lower surface: Red-Purple Group 62C.

*Upon opening, inner petals*.—Upper surface: Red-Purple Group 62A. Lower surface: Red-Purple Group 62B.

*Basal petal spots, upon opening*.—Upper surface: Yellow-Orange Group 19A. Lower surface: Yellow-Orange Group 19A.

*After opening, outer petals*.—Upper surface: Red-Purple Group 62C. Lower surface: Red-Purple Group 62D.

*After opening, inner petals*.—Upper surface: Red-Purple Group 62A. Lower surface: Red-Purple Group 62B.

*Basal petal spots, after opening*.—Upper surface: Yellow-Orange Group 19B. Lower surface: Yellow-Orange Group 19B.

Petals:

*Petal reflex*.—Outer petals have moderate reflex.

*Margin*.—Entire and uniform. No undulations.

*Shape*.—Broad elliptic. Apex shape: Rounded. Base shape: Rounded.

*Size*.—30 mm (l)×30 mm (w).

*Texture*.—Smooth.

*Thickness*.—Average.

Petaloids:

*Size*.—19 mm (l) by 10 mm (w).

*Quantity*.—About 10.

*Shape*.—Irregular, asymmetric, with an acute base and acute apex.

*Color*.—Upper surface is Red-Purple Group 62A. Lower surface is Red-Purple Group 62B. Petaloid spot on upper and lower surface is Yellow-Orange Group 19B.

Reproductive flower parts:

*Pollen*.—None observed.

*Anthers*.—Size: 2 mm in length. Color: Yellow-Orange Group 22A. Quantity: 100 on average.

*Filaments*.—Color: Yellow Group 12A. Length: 5 mm.

*Pistils*.—Length: 4 mm. Quantity: About 40.

*Stigmas*.—Color: Greyed-Yellow Group 1C.

*Styles*.—Color: Red Group 47B.

*Location of stigmas*.—Level in location relative to the length of the filaments and the height of the anthers.

*Hips*.—None Observed.

PLANT

Plant growth: Upright, bushy. Plants are 25 cm in height, and 30 cm wide.

Stems:

*Color*.—Juvenile growth: Yellow-Green Group 144B. Mature growth: Yellow-Green Group 146A.

*Length*.—On average, canes are 20 cm from the base of the plant to the flowering portion.

*Diameter*.—4 mm.

*Internodes*.—On mature canes about 35 mm between nodes.

*Surface texture*.—Young wood: Smooth. Older wood: Smooth.

Long prickles: None observed.

Plant foliage:

*Compound leaf*.—About 85 mm (l)×65 (w).

*Quantity*.—3 to 4 leaves per 10 cm of stem on average.

*Leaf bearing angle to the stem.*—45 degrees.

*Color of juvenile foliage*.—Upper side: Yellow-Green Group 146A with marginal intonations of Greyed-Purple Group 183B. Lower side: Yellow-Green Group 146C.

*Color of mature foliage*.—Upper side: Yellow-Green Group 147A. Lower side: Yellow-Green Group 147C.

Plant leaves and leaflets:

*Stipules*.—Size: 9 mm long, 2 mm wide. Quantity: 2 per compound leaf. Shape: Linear, slightly broad based with outward extending apices. Margins: Finely serrated. Color: Yellow-Green Group 147A with intonations of Red-Purple Group 183B.

*Petiole*.—Length: 15 to 20 mm. Diameter: 2 mm. Upper surface color: Yellow-Green Group 147B. Lower surface color: Yellow-Green Group 146A.

*Rachis*.—Length: 10 to 25 mm. Upper surface color: Yellow-Green Group 147B. Lower surface color: Yellow-Green Group 146A. Observations: Small prickles.

*Leaflet*.—Quantity: Normally 5 leaflets. Margins: Serrated. Size: Terminal leaflets are 30 to 45 mm long, 17 to 25 mm wide. Shape: Generally ovate. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar094', substantially as illustrated and described herein, due to its abundant deep pink flowers, disease resistance, and extended period of bloom.

* * * * *

'Poulpar094'

'Poulpar094'

'Poulpar094'